United States Patent [19]

Perfect

[11] 4,185,740
[45] Jan. 29, 1980

[54] DISPOSABLE CAPSULES

[75] Inventor: Alan J. Perfect, Allentown, N.J.

[73] Assignee: Johnson & Johnson, New Brunswick, N.J.

[21] Appl. No.: 930,343

[22] Filed: Aug. 2, 1978

[51] Int. Cl.² .............................................. B65D 81/32
[52] U.S. Cl. ................................................... 206/220
[58] Field of Search ......................... 206/219, 220, 221

[56] References Cited

U.S. PATENT DOCUMENTS

| | | | |
|---|---|---|---|
| 3,139,180 | 6/1964 | Kobernick | 206/220 |
| 3,796,303 | 3/1974 | Allet-Coche | 206/220 |
| 3,963,120 | 6/1976 | Perfect | 206/219 |

Primary Examiner—Donald F. Norton

[57] ABSTRACT

The instant invention relates to disposable capsules which contain coreactive components in separate chambers and means for automatically combining and mixing said coreactive components prior to opening the capsule. The instant disposable capsules may contain dental amalgam precursors such as mercury and silver which may be combined and mixed merely by placing such capsule in a dental amalgamator. The disposable capsules comprise a hollow cylindrical section closed at one end and having an internal constriction spaced from the other end, and a movable insert comprising a stem having an upper portion inserted through and frictionally engaging said constriction and a flange extending outwardly about the lower end of said stem and frictionally engaging the inner wall of the hollow cylindrical section, whereby said flange initially divides said cylinder into two noncommunicating chambers.

14 Claims, 7 Drawing Figures

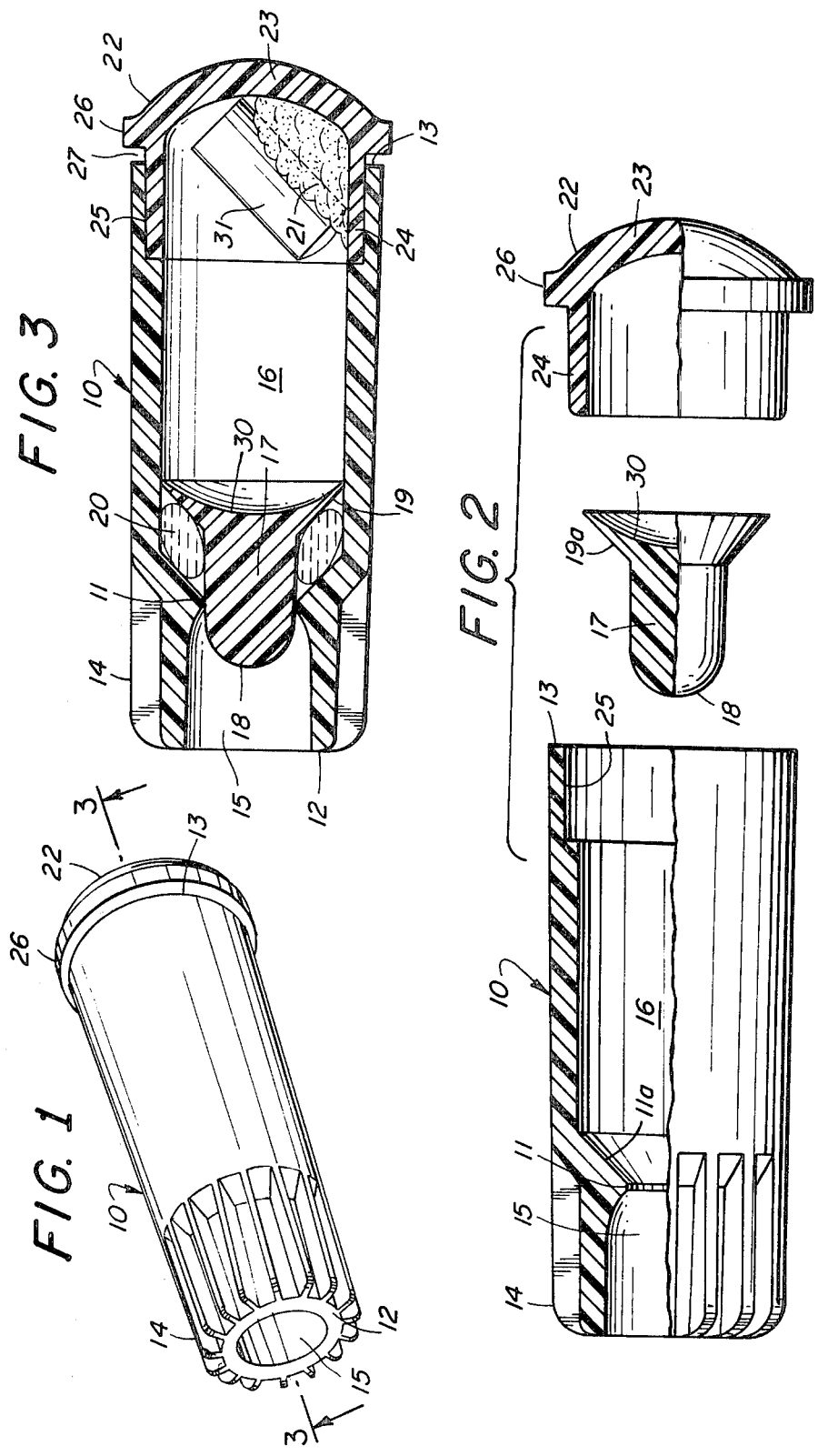

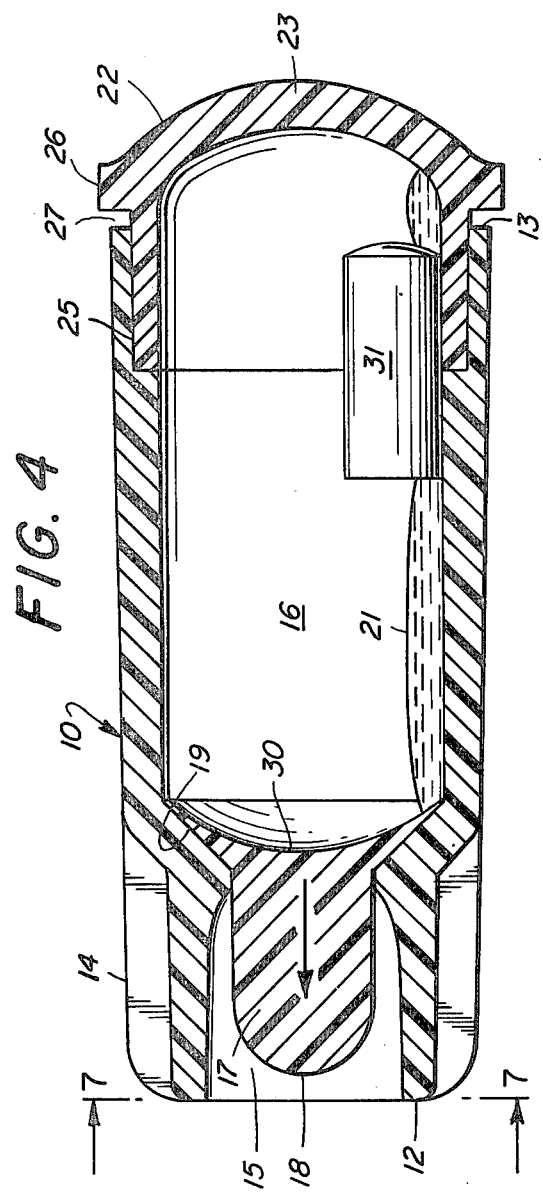
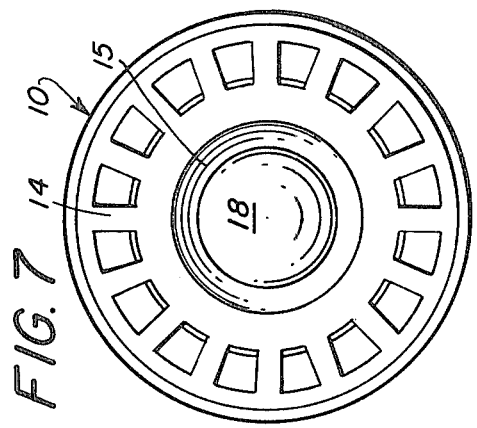
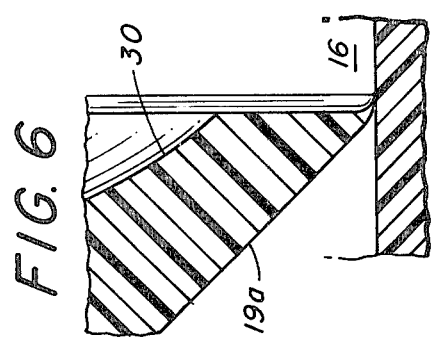
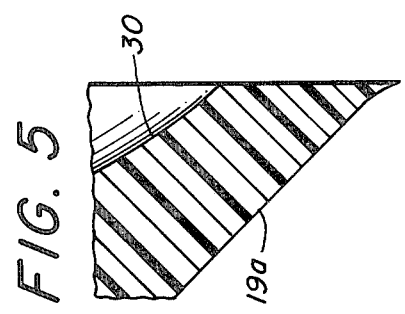

DISPOSABLE CAPSULES

BACKGROUND OF THE PRIOR ART

Disposable capsules useful to maintain coreactive components, are known in the art. For example, dental capsules containing amalgam precursors as mercury and silver or silver alloy are well known. In all of the prior art disposable capsules, a manipulative step must be carried out prior to mixing the coreactive components.

It would be very desirable to eliminate any such manipulative step and especially in the dental art it would be desirable to have a dental capsule containing the dental amalgam precursors from which a dental amalgam could be prepared merely by placing such capsule into an amalgamator.

Examples of prior art of disposable capsules include capsules having rupturable membranes and means for rupturing said membranes prior to mixing of coreactive components. For example, U.S. Pat. No. 3,451,540 teaches a disposable capsule comprising a telescoping cylinder which is activated by sliding the separate section together to rupture the membrane which divides the capsule into two chambers and thereby allow the coreactants maintained separate in such chambers to mix. Similar capsules are disclosed in U.S. Pat. No. 3,625,349 and U.S. Pat. No. 3,595,439 wherein the membrane is in the form of a pouch, containing a coreactant and such pouch is ruptured by either squeezing through a rotating mechanism or a sliding mechanism until it bursts. See also U.S. Pat. Nos. 3,907,106, 3,860,114, 3,841,467, 3,831,742, 3,655,035, 3,638,918, 3,756,571, 1,774,258 for similar capsules.

Disposable capsules which utilize a removable plug to isolate the coreactive components and which plug is removed to allow such components to mix are also known in the art. See for example U.S. Pat. No. 3,275,302, wherein a ball or a disc is positioned to divide the capsule into two chambers each containing a coreactive component. This capsule is activated by turning the capsule upside down to dislodge the ball or disc. See also U.S. Pat. Nos. 3,796,303, 3,809,225, 2,527,992, 2,527,991 and 3,785,481 for other capsules utilizing removable plugs.

Other disposable capsules rely on a passageway between the two chambers which passageway can be closed and opened by either twisting, sliding or unscrewing one or more sections of the capsule. For example, in U.S. Pat. No. 3,357,545 the top of the capsule is unscrewed to remove a stem on the upper section of said capsule from a conduit in the lower section. Removal of such stem allows the coreactive component maintained in the upper section to fall into the lower section. Also see U.S. Pat. Nos. 3,139,180, 3,139,181, 3,917,062, 3,963,120 and 3,924,741 for similar capsules.

It is thus clear that unlike the instant disposable capsule, the prior art capsules require some manipulative step prior to the step of mixing the coreactive components.

SUMMARY OF THE INSTANT INVENTION

The instant invention relates to a capsule divided into two chambers by slidable barrier means said slidable barrier means movable from a first position to a second position by a force from within said capsule directed against such slidable barrier when said capsule is shaken, said chambers being capable of holding coreactive components separate while said slidable barrier is in said first position and said chambers being in communication when said slidable barrier means is in said second position.

More particularly, the instant invention relates to a disposable capsule comprising (1) a hollow cylindrical section having an axially located shoulder spaced from the ends of the cylinder such that the internal diameter of such cylinder at a point spaced from its ends is thereby provided with a constriction; (2) a plug being detachably secured to the lower end of said hollow cylindrical section; and (3) an insert comprising a stem having an upper portion which is inserted through and frictionally engages said constriction and a flange extending outwardly about the lower end of said stem, said flange being spaced from said shoulder and said plug and being frictionally engaged with the inner wall of said hollow cylindrical section along the entire periphery thereof, whereby said cylinder and said plug forms a mixing chamber and said flange divides said mixing chamber into two non-communicating chambers.

This disposable capsule is especially suited for packaging dental amalgam precursors such as mercury and silver alloy tablet or powder. The mercury will be contained in the chamber wherein the stem is located (upper chamber) and powder will be contained in the other (lower chamber). The capsule may include a pestle in the (lower) chamber, said pestle being of sufficient weight and dimension whereby upon shaking, the pestle will act on said flange to cause it to move further toward the constriction of said hollow cylindrical section. Upon such movement, the stem will be forced past said constriction until the flange mates with said shoulder. The volume of the upper chamber is decreased thereby compressing the mercury until it is forced past the edge of said flange into the lower, powder containing chamber. Preferably, the edge of said flange is tapered to ease the passage of mercury into the lower chamber. Preferably the surface of flange toward such constriction is shaped to nest with the shoulder of said upper chamber. For example, the surface of said flange (excluding the valve stem) toward such upper chamber may be conical in shape and the shoulder angled in a complementary configuration. This configuration assures that all of the mercury will be forced into the powder chamber and utilized in the amalgam. It will be appreciated that residual mercury, i.e., mercury not used in the amalgam must be kept at a low level for economy as well as minimize safety problems in disposing of the used capsules.

The user, i.e., the dentist or dental technician, can activate the instant capsule merely by placing said capsule in the standard amalgamator.

Because no separate manipulative step is necessary to combine the coreactive components other than placing the capsule in an amalgamator, the user is assured of effective communication between the two chambers. In the prior art, devices employing a screwing action to allow such communication, one could unscrew the upper portion through 360° or more and still not be certain that complete combination of the mercury with the silver alloy had taken place. In those employing a pulling or pushing action, the large amount of frictional resistance to the pulling or pushing made it uncertain whether complete removal of the occlusion between the chambers had occurred. These uncertain and time consuming procedures are eliminated in the container of the present invention because communication between the two chambers is obtained by the amalgamator alone.

Furthermore, unlike many of the prior art capsules, the design of the capsule of the present invention requires no screwing to function. Thus the manufacture thereof is simplified. Because no screw threads need be formed, the tolerances to which the parts of the container must be manufactured are less rigid. Furthermore, the materials from which the container of the invention may be manufactured (discussed below) are more easily and economically formed than those from which the containers of the prior art must be manufactured. Hence these containers are more economical to manufacture than those of the prior art, all other factors being equal.

BRIEF DESCRIPTION OF THE FIGURES

FIG. 1 shows an exterior view of the instant capsule.

FIG. 2 shows a cross section view of the capsule prior to activation.

FIG. 3 shows an exploded view of the instant capsule.

FIG. 4 shows a cross sectional view of the capsule after activation and mixing.

FIG. 5 shows the periphery of the flange in cross section.

FIG. 6 shows the relationship of the periphery of the flange and the internal walls of the instant capsule.

FIG. 7 shows the end view of the instant capsule as taken from line 7—7'.

DETAILED DESCRIPTION OF THE FIGURES

Referring now in greater detail to the figures, the capsule of the instant invention comprises a hollow cylindrical section (10) having an axially located shoulder (11) spaced from the upper end (12) and the lower end (13) of section (10) such that the internal diameter of section (10) at a point spaced from ends (11) and (12) is provided with a constriction.

In the preferred embodiment shown in FIG. 1, it is noted that the upper portion of section (10) is provided with ribs (14) which aid the gripping of said capsule in the amalgamator and allow ease of molding the capsule. The ribs are oriented radially about the upper portion of section (10) and in an equidistant manner. In the embodiment shown, 16 ribs are provided, however, greater and lesser amounts are suitable depending on esthetics, design considerations and amount of distortion and sink which can be tolerated during fabrication of the capsule.

The ribs are curved at the upper end (12) of section (10) and extend toward said lower end (13) and merge into the walls of section (10) at a point proximate said shoulder (11).

The shoulder (11) divides the internal volume of section (10) into a stem receiving chamber (15) toward the upper end of said section (10) and a chamber (16) for retaining the coreactive components toward said lower end of section (10).

An insert (17) having a stem (18) and a flange (19) is positioned in chamber (16) to divide said chamber (16) into two chambers for separately containing coreactive components. The periphery of flange (19) conforms in shape to the internal diameter of chamber (16) although of somewhat greater dimension and is generally circular and disclike. As shown, the flange (19) is located about the lower end of stem (18) and engages the internal wall of chamber (16) in a sealing manner. The stem (18) frictionally engages said shoulder (11) towards its upper end in a sliding fit. The material of the insert is resiliently flexible whereby the flange provides an adequate seal between said coreactive component containing chambers (20) and (21) while allowing the insert to move back toward the upper end of section (10). Preferably, insert (17) is an integrally molded thermoplastic such as low density polyethylene, polyester e.g., HYTREL and polyacetal, e.g. DELRIN.

The shoulder (11) may be of any shape whereby it axially engages said stem (18) in a sealing manner yet will not prohibit the sliding of the stem as said insert is forced toward said upper end (12). In the preferred embodiment shown, the shoulder is frustoconical in cross-section with the plane engaging the stem. Of course, the shoulder may be rounded or pointed in cross-section, however, it has been found that the frustoconical cross-section provides the best balance of sealing with sliding functions.

It should be pointed out that the sealing function of shoulder (11) is not as critical as the sealing function of flange (19) since leakage at the shoulder would only allow the reactive component to pass into the environment while leakage at the flange might result in the premature reaction of the coreactive components. However, when mercury is contained in chamber (20) it is critical for safety reasons that the shoulder provide at least as effective a seal as the flange.

As will be apparent, the insert is positioned in section (10) in a manner to provide said chambers (20) and (21) with adequate volumes for holding the required amounts of coreactive components. The relative volumes of chambers (20) and (21) can be adjusted by the positioning of insert (17). Chamber (20) is especially suitable for holding liquid coreactive components such as mercury. Chamber (21) will generally contain either a liquid or a powder coreactive component such as silver or silver alloy. As noted above, the instant capsule functions by moving the insert back toward the upper end of section 10 to diminish the volume of chamber (20) with a corresponding increase in the volume of chamber (21) to thereby force the coreactive component (liquid) contained therein into chamber (21). In order to provide adequate force to move said insert in the aforesaid manner, as well as to assist in mixing the coreactive components, a pestle is provided in chamber (21). The dimensions of chamber (21) along the long axis is substantially greater than chamber (20) so as to allow the pestle to generate greater force during the shaking in the amalgamator.

Chamber (21) is sealed with a plug (22) which is detachably secured to the lower end of section (10).

The plug (22) as shown has a hemispherically shaped lower end (23) integral with a hollow cylindrical upper end (24) which telescopically engages an axially extending groove (25) located about the lower end of section (10). In the preferred embodiment the plug (22) is joined to section (10) in a flush manner to provide a smooth internal surface for chamber (21). It has been found that increasing internal surface irregularity results in higher residuals of both the coreactive components and the reaction product thereof remaining in the capsule after use. Besides the obvious economy disadvantage in having increased residuals, the environmental contamination problems of disposing of used capsules containing mercury or other noxious substances will be apparent.

Other means for detachably securing said plug (22) to section (10) will be obvious to one skilled in the art, e.g., screwing means, snapfit, pushfit, etc., however, for the purpose of providing a regular internal surface for chamber (21) the aforedescribed method is preferred.

As shown, the plug may be provided with an external axially extending ridge (26) to facilitate detachment from section (10). Note also that in the preferred embodiment shown the hollow cylindrical upper end (24) of the plug is dimensioned to be greater in height than the length of axially extending groove (25). This structural relationship provides an external, axially extending groove (27) adjacent said ridge (26) for additional ease of detaching said plug with a thin instrument or a fingernail.

To return to the relationship of the insert (17) to the section (10), it will be apparent from the figures that the length of the stem is preferably less than the distance between said shoulder (11) and said upper end (12), i.e., the length of the stem receiving chamber (15).

To ensure the maximum passage of the reactive component contained in chamber 20 into chamber 21, it is desirable that the flange be forced toward the upper end of section (10) until the upper surface (19a) of said flange engages the shoulder (11). The stem must, therefore, not be of such length as to be blocked from lateral movement by the grips of an amalgamator thereby preventing said flange to engage said shoulder. The easiest way to ensure that the lateral movement of the insert will not be restricted by any of the amalgamator grips available to the destist or other dental practioner is to maintain the length of the stem less than the length of the stem receiving chamber.

Also as a further safeguard against mercury passing the seal provided by said shoulder (11) into the environment, a removable tape or plug (not shown) can be used to seal the upper end of said section (10). If such a removable tape or plug is utilized, an air vent may be provided in said tape or in the walls of said stem receiving chamber (15) to prevent the formation of an airlock to hinder movement of the stem into said chamber (15). An air vent might also be provided in the walls of said chamber (20) proximate shoulder (11) to prevent an airlock restricting the movement of flange (19) toward said shoulder.

An additional structural feature of instant capsule is provided by the shaping of the upper surface of the flange to conform to the lower surface (11a) of the shoulder (11). This feature ensures mating of said surfaces and a greater degree of passage of the reactive component from chamber (20) to (21) since at the conclusion chamber (21) will be substantially equivalent in volume to the combined volumes of chambers (20) and (21) and the volume of chamber (20) will be essentially nonexistent. This relationship is shown most clearly in FIG. 4.

The capsule may be activated by shaking in a dental amalgamator wherein the capsule is agitated along the direction perpendicular to the plane of said flange. The pestle will strike the lower surface of the flange and force the flange back toward the shoulder of the hollow cylindrical section. As can be seen in FIG. 4, the mercury is squeezed past the periphery of the flange. To facilitate passage of mercury, the periphery of the flange is preferably of reduced thickness as compared to the general thickness of the flange, i.e., the periphery is tapered (see FIG. 5).

In the typical dental capsule, i.e., of dimensions of 1 to 1¼ inches by approximately ½ inch, the stem receiving chamber (15) may have a length of 0.16", chamber (20) may have a length of 0.133", and chamber (21) may have a length of 0.81" (prior to activation).

Furthermore, the lower surface (30) of the flange may be concave whereby the concave center tends to direct the force of the moving pestle uniformly across the flange thereby minimizing "cooking" as the flange moves toward the upper end of said hollow cylindrical section.

After mixing, the capsule may be pulled apart to obtain the amalgam.

The instant dental capsule is of an external dimension suitable for placement in the grips of a dental amalgamator, i.e., the ends are like the prior art dental capsules hemispherically shaped. The hollow cylindrical section and the plug may be formed from any material which is inert to the correactive components contained therein. For ease of fabrication, a thermoplastic, such as, polycarbonate may be used. In general, the hollow cylindrical sections should be made of rigid material such as metal, plastic, or the like. In the preferred embodiment, they are made of rigid, thermoplastic material such as, for example, polycarbonate, polyacrylic, polyvinyl chloride, or the like. The material of choice is polycarbonate with a high density polyethylene plug.

The plug, the insert and the hollow cylindrical section are preferably formed by injection molding, by any suitable technique for forming the materials may be employed.

The use or rigid material for the hollow cylindrical section and the plug minimizes retention of mercury in the capsule. Further, this combination of rigid materials and a flexible insert requires less strict manufacturing tolerances because the flexible material of the disc will adjust to minor deviations in the structure of the hollow cylindrical section leading to more economic and efficient manufacture of the capsule of the invention.

To fill the dental capsule of the instant invention, insert (17) is positioned in the hollow cylindrical section (10) toward the lower end of section (10) whereby stem (18) is not engaged by said shoulder (11) yet the flange (19) is in sealing engagement with the internal walls of section (10). Mercury is passed into said section (10) through the valve receiving chamber (15) and the insert (17) is moved towards the upper end of section (10) until said stem (18) engages shoulder (11) in a sealing manner. The removable tape or plug may be applied to the upper end of section (10) at this point. Plug (22) may be filled with silver or silver alloy, in either powder or tablet form, a pestle placed therein, and secured to the lower section of section (10). Alternatively, the silver or silver alloy and/or the pestle may be placed in chamber (16) after the mercury has been sealed into chamber (20) and the plug secured to section (10).

According to the invention, the premeasured components can be mixed without being touched or measured by the user in a more accurate and simple fashion than previously known. It should be understood that while the container of the invention has been exemplified in the mixing of dental amalgam, other dental compositions such as acrylate polymer dental filling materials may be packaged and mixed therein. Further, the container may be used in fields other than dentistry where ingredients must be kept separate until just prior to use, as for example, in the prepackaging of epoxy resins and accelerators for the formation of cements.

The scope of the present invention is not to be limited to the specific embodiment shown herein, which is for purposes of illustration only. Many modifications and deviations may be made therefrom without departing from the scope of the present invention, which scope is defined only in the appended claims.

What is claimed is:

1. A disposable capsule comprising (1) a hollow cylindrical section, said hollow cylindrical section having an axially located shoulder spaced from the ends of the cylinder such that the internal diameter of such cylinder at a point spaced from its ends is thereby provided with a constriction; (2) a plug being detachably secured to the lower end of said hollow cylindrical section; and (3) an insert comprising a stem having an upper portion which is inserted through and frictionally engages said constriction and a flange extending outwardly about the lower end of said stem, said flange being spaced from said shoulder and said plug and being frictionally engaged with the inner wall of said hollow cylindrical section along the entire periphery thereof, whereby said cylinder and said plug forms a mixing chamber and said flange divides said mixing chamber into two non-communicating chambers.

2. The capsule of claim 1 wherein the edge of said flange is tapered around the entire periphery thereof.

3. The capsule of claim 1 including radially oriented equidistantly spaced ribs about upper portion of the hollow cylindrical section.

4. The capsule of claim 3 wherein said ribs are curved toward the upper end of said hollow cylindrical section, extend toward the lower end of hollow cylindrical section and merge with the walls thereof at a point proximate said shoulder.

5. The capsule of claim 1 wherein said shoulder divides the internal volume of said hollow cylindrical section into an upper stem receiving chamber and a lower chamber for retaining a coreactive component.

6. The capsule of claim 5 wherein said stem is lesser in length than the length of said stem receiving chamber.

7. The capsule of claim 1 wherein the periphery of said flange is disc like and of greater dimension than the internal diameter of said hollow cylindrical section.

8. The capsule of claim 1 wherein said insert is made of a resiliently flexible material.

9. The capsule of claim 1 wherein said shoulder is frusto conical in cross section.

10. The capsule of claim 1 wherein said hollow cylindrical section includes an axially extending groove about its lower end.

11. The capsule of claim 10 wherein said plug includes a hemispherically shaped lower end and a hollow cylindrical upper end which is dimensioned to telescopically engage the axially extending groove of said hollow cylindrical section.

12. The capsule of claim 1 wherein said plug includes an external axially extending ridge.

13. The capsule of claim 1 wherein the upper surface of said flange conforms in shape to the lower surface of said shoulder.

14. A capsule divided into two chambers by slidable barrier means, said slidable barrier means movable from a first position to a second position by a force from within said capsule directed against such slidable barrier when said capsule is shaken, said chambers being capable of holding coreactive components separate while said slidable barrier is in said first position and said chambers being in communication when said slidable barrier means is in said second position.

* * * * *